United States Patent
Pessala et al.

(10) Patent No.: US 6,443,150 B1
(45) Date of Patent: Sep. 3, 2002

(54) ANAESTHETIC VAPORIZER

(75) Inventors: Tom Pessala, Bromma; Pär Emtell, Vällingby, both of (SE)

(73) Assignee: Siemens Elema AB, Solna (SE)

( * ) Notice: Subject to any disclaimer, the term of this patent is extended or adjusted under 35 U.S.C. 154(b) by 38 days.

(21) Appl. No.: 09/657,606

(22) Filed: Sep. 8, 2000

(30) Foreign Application Priority Data

Sep. 9, 1999 (SE) .............................................. 9903193

(51) Int. Cl.⁷ .............................................. A61M 15/00
(52) U.S. Cl. .............................. 128/203.14; 128/203.12; 128/203.25
(58) Field of Search ........................ 128/203.12, 203.13, 128/203.14, 203.19, 203.24, 203.25, 204.18, 204.21, 205.24, 200.24

(56) References Cited

U.S. PATENT DOCUMENTS 5,771,882 A * 6/1998 Psaros et al. .......... 128/203.12
6,220,242 B1 * 4/2001 Wallin .................... 128/203.12
6,286,505 B1 * 9/2001 Psaros .................... 128/203.12

FOREIGN PATENT DOCUMENTS

| EP | 0 469 797 | 2/1992 |
| EP | 0 720 858 | 7/1996 |

* cited by examiner

Primary Examiner—Glenn K. Dawson
(74) Attorney, Agent, or Firm—Schiff Hardin & Waite

(57) ABSTRACT

An anaesthetic vaporizer for dosing a liquid anaesthetic has a liquid container for the anaesthetic, and outlet tube from the liquid container to a dosing point, a first regulator for regulating a flow of anaesthetic from the liquid container toward the dosing point and a control unit for controlling dosing. To improve dosing and safety, the anaesthetic vaporizer has a return tube connected in parallel across the first regulator by a first connection point, downstream from the first regulator, and a second connection point, upstream from the first regulator, a second regulator is arranged in the return tube and a third regulator is arranged in the outlet tube, downstream from the first connection point. The control unit controls at least one of the regulators in dosing the anaesthetic.

10 Claims, 2 Drawing Sheets

ANAESTHETIC VAPORIZER

BACKGROUND OF THE INVENTION

1. Field of the Invention

The present invention relates to an anaesthetic vaporizer.

2. Description of the Prior Art

An anaesthetic is usually administered to patients who, for various reasons, are about to undergo surgery or an examination. In inhalation anaesthesia, a gas mixture of oxygen and nitrous oxide are usually administered along with an anaesthetic. The anaesthetic is in liquid form and must be vaporized before it reaches the patient. Dosing and vaporization normally take place in an anaesthetic vaporizer.

A number of different types of vaporizers are known. One way to dose and vaporize liquid anaesthetic is to draw some of the gas mixture through the liquid, causing it to pick up anaesthetic vapor. Another way is to draw part of the gas mixture over the surface of the liquid anaesthetic. The surface area of this liquid can be enlarged with the aid of wicks which draws up the liquid.

Dosing in these vaporizer types is usually based on the saturation of gas, drawn over or through the liquid, with vaporized anaesthetic. Dosing is affected by factors such as temperature and pressure, in addition to problems in ensuring that saturation really does take place.

In another type of vaporizer, the liquid is first boiled or transformed into vapor in some other way. The vapor is then dosed via valves into the gas mixture supplied to the patient. Problems may occur in e.g. maintaining a constant pressure for the anaesthetic vapor (variations in pressure affect dosing).

A third version is to inject a dosed amount of liquid into the gas flow (directly or through a filter of some kind).

Dosing can be regulated by pressurization of the liquid or by pumping specific quantities of the liquid from a liquid container.

If a pump is used, it is essential for the pump to be exact and rugged. Pressure also plays an important role. The pump's ability to pump the correct amount of liquid can be affected by pressure in the liquid container which, in turn, can be affected by the egress of liquid. Liquid held in the tubing between the liquid container and the pump also presents a problem.

SUMMARY OF THE INVENTION

An object of the invention is to achieve a rugged and reliable anaesthetic vaporizer that avoids the problems associated with known anaesthetic vaporizers, as described above.

The above object is achieved in accordance with the principles of the present invention in an anaesthetic vaporizer for dosing a liquid anaesthetic having a liquid container for the anaesthetic, an outlet tube proceeding from the liquid container to a dosing point, a first regulator for regulating the flow of anaesthetic from the liquid container toward the dosing point, a control unit for controlling dosing of the anaesthetic, a return tube connected in parallel across the first regulator at a first connection point downstream from the first regulator and at a second connection point upstream from the first regulator, a second regulator connected in the return tube, and a third regulator connected in the outlet tube, downstream from the first connection point. The control unit controls at least one of the first, second and third regulators for controlling dosing of the anaesthetic.

Connecting a return tube in parallel across the first regulator e.g. a pump, makes it easier to control pressure downstream from the pump. The second regulator is arranged in the return tube and the third regulator in the dosing tube. The control unit can dispense anaesthetic in a safe and accurate manner by controlling at least one of the regulators.

In an embodiment of the anaesthetic vaporizer according to the invention, the second regulator is an additional pump, and the third regulator is a dosing restriction. Pressure before the dosing restriction can be accurately regulated by regulating the pumps, flow through the dosing restriction thereby achieving great accuracy. Regulating one of the pumps is sufficient if the other pumps at a constant rate.

Alternatively, or as a complement, the dosing restriction can be variable. The control unit can then control the dosing restriction to compensate for any pressure variations occurring when there are rapid changes in dosing.

In another embodiment of the anaesthetic vaporizer according to the invention, the second regulator is a back-flow restriction and the third regulator is a dosing valve. The dosing valve can be controlled by the control unit according to the pressure, so the correct dosing is achieved. The pump can simultaneously be controlled to maintain the pressure.

As an alternative or a complement in this embodiment, the back-flow restriction can be variable.

The second connection point of the return tube can be arranged in the outlet tube upstream from the pump. The second connection point alternatively can be arranged at the liquid container.

The liquid container can be devised with a venting device in order to regulate the negative pressure in the container. It should be devised to minimize the risk of leakage of anaesthetic into the atmosphere.

Additional control of dosing (and an opportunity to increase accuracy) is achieved by arranging a flow meter in the outlet tube downstream from the first connection point.

A pressure stabilizer can be connected to the outlet tube, downstream from the first connection point, in order to enhance the maintenance of pressure downstream from the pump.

Arranging an anaesthetic meter to measure the anaesthetic content of the gas mixture increases safety and improves opportunities for refining dosing control.

Safety can also be increased by arranging a shut-off valve in the outlet tube downstream from the second regulator.

DESCRIPTION OF THE PREFERRED EMBODIMENTS

Figure 1:
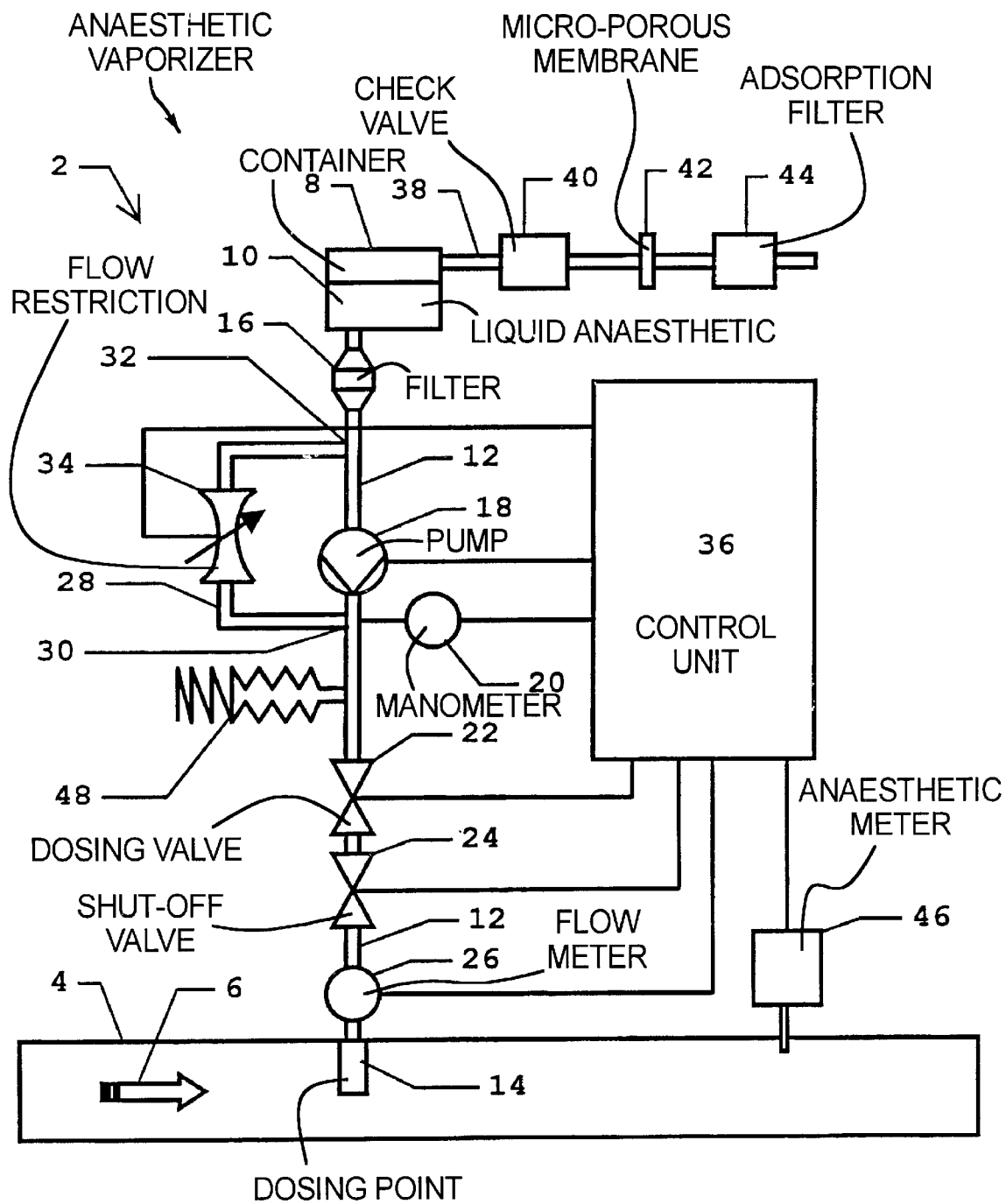
FIG. 1 shows a first embodiment of the inventive anaesthetic vaporizer.

FIG. 1 is a schematic depiction of an anaesthetic vaporizer 2 according to the invention for dosing anaesthetic into a tube 4 in which a gas mixture flows (according to the arrow 6). Tube 4 can be a part of a fresh gas system or a breathing circuit (re-breathing or non re-breathing).

The anaesthetic vaporizer 2 has a liquid container 8 holding liquid anaesthetic 10 for dosing. The anaesthetic 10 consists primarily of one of the anaesthetics desflurane, enflurane, halothane, isoflurane or sevoflurane.

An outlet tube 12 for the anaesthetic 10 proceeds from the liquid container 8. The outlet tube 12 leads to a dosing point 14 in the tube 4. The dosing point 14 can be devised in a suitable fashion to facilitate vaporization of the anaesthetic 10. For example, it can have a nozzle, preferably a rotating nozzle, arranged on the end of the outlet tube 12.

The liquid anaesthetic 10 alternatively can be carried to a filter or some other porous structure made of a suitable material (sintered metal, mesh, porous plastic, a membrane, activated charcoal etc.). Heat can also be applied to the dosing point 14 to facilitate vaporization.

A number of components are arranged in the outlet tube 12. A filter 16 is arranged immediately downstream from the liquid container 8. The purpose of this filter 16 is simply to filter particles and dirt out of the system that otherwise could disrupt dosing.

A pump 18 is arranged downstream from the filter 16. The pump 18 pumps liquid anaesthetic 10 from the liquid container 8. Operation of the pump 18 in dosing is described in more detail below.

A manometer 20, a dosing valve 22, a shut-off valve 24 and a flow meter 26 are arranged downstream from the pump 18. The function and purpose of these components are described below in detail.

A return tube 28 in parallel across the pump 18 is connected to the outlet tube 12 at a first connection point 30 and a second connection point 32. In this embodiment, the first connection point 30 is arranged between the pump 18 and the dosing valve 22. The second connection point 32 is arranged between the filter 16 and the pump 18. A back-flow restriction 34 is arranged in the return tube 28. The back-flow restriction 34 can be fixed or variable. FIG. 1 shows the latter version. The back-flow restriction 34 alternatively can be replaced with a pressure regulator.

The anaesthetic vaporizer 2 is controlled by a control unit 36. Control can be exercised in any of the following ways (or versions thereof).

One way to control the anaesthetic vaporizer 2 to dose the desired amount of liquid anaesthetic 10, is based on controlling the pump 18 so as to maintain a pre-set pressure between the pump 18 and the dosing valve 22. This control can be exercised regardless of the pressure measured by the manometer 20.

The flow-through performance of the dosing valve 22 at the prevailing pressure is known, i.e. the amount of liquid flowing through the dosing valve 22 at the prevailing pressure is known. When the dosing valve 2 is regulated, a specific amount of liquid anaesthetic can therefore be dosed. The dosing valve 22 can be e.g. an ON/OFF valve controlled with a duty cycle supplying the correct dosing for the prevailing pressure and the set dose.

The pressure drops a little when the dosing valve 22 opens to dose a specific amount. When a fast-acting manometer 20 is used, the pump 18 is able to respond with corresponding swiftness in restoring pressure without affecting flow through the dosing valve 22.

Operating pressure between the pump 18 and the dosing valve 22 can be affected by the variable back-flow restriction 34 also. Pressure changes in the system can be performed more rapidly by changing the degree of restriction. Greater operating point dynamics and, accordingly, greater dosing dynamics can therefore be achieved.

With the variable restriction 34, the pump 18 can be allowed to run at a constant speed. Pressure can then be maintained by merely controlling the variable restriction 34.

An alternative is to allow pressure to drop somewhat during the dosing of liquid anaesthetic. This can be achieved by e.g. having the pump 18 operate with a constant pump output and using a fixed back-flow restriction 34. The measured pressure curve then becomes saw-toothed. The drops in pressure are then proportional to the amount dosed. The amount dosed can therefore be determined from the drops in pressure.

The amount dosed also can be checked by measuring the dosed flow with the flow meter 26. The flow meter 26 does not need to be placed next to the dosing point 14 but can be located anywhere in the outlet tube downstream from the first connection point 30.

If the amount dosed deviates excessively from the reference amount, supply can be stopped completely by closing the dosing valve 22 or the shut-off valve 24. Shut-off valve 24 can therefore be placed upstream dosing valve 22 as an alternative. Even if the figure shows that the measurement signal from the flow meter 26 goes to the control unit 36, this safety feature can be completely separate from the dosing control exercised by the control unit 36.

Access to the flow signal also provides scope for more refined regulation of dosing. The different control parameters, i.e. pressure, flow, pump output, back-flow restriction, the opening of the dosing valve or its duty cycle, can all be given different emphases in order to achieve optimal dosing. For example, a neural network could be gradually taught to control dosing.

Regardless of which of these methods is used, the anaesthetic vaporizer according to the invention conveys specific advantages. It is, generally speaking, easier to dose liquids than gases since liquids are virtually non-compressible. The two-stage system with the pump in series with the valve, in combination with back-flow via restriction, improves control over operating conditions, such as working pressure etc. Even if the pressure in the liquid container 8 varies (is higher or lower than the operating pressure), this does not, in principle, affect dosing.

In those instances in which there is positive pressure in the liquid container 8, the pump 18 can be replaced with a valve, but the back-flow restriction 34 should then be replaced with a pump at the same time in order to ensure that back-flow can occur.

Negative pressure will develop in the liquid container 8 with most anaesthetics as liquid is pumped out. Imposing a limit on this negative pressure may be appropriate. If negative pressure becomes excessive, an increasingly powerful pump 18 will be needed to maintain the working pressure downstream from the pump 18.

One way to limit the negative pressure is shown in FIG. 1. An air tube 38 is connected to the liquid container 8 and leads to atmosphere. A check valve 40 opens, at a fixed or pre-set pressure gradient between atmosphere and pressure in the liquid container 8, to admit air. Alternatively, a pressure regulator or valve, controlled by the pressure measured in the liquid container 8, can be used.

A micro-porous membrane 42 is also arranged in the air tube 38. The membrane 42 passes air but not liquid. The membrane 42 therefore prevents liquid anaesthetic from escaping into atmosphere.

If anaesthetic vapor does pass the membrane 42, an adsorption filter 44 is also arranged in the air tube 38. The adsorption filter 44 can be devised to adsorb anaesthetic vapor which would otherwise escape to the atmosphere and desorbs the vapor when the valve 40 opens to the passage of a flow of air from the atmosphere. The anaesthetic vapor is then returned to the liquid container 8. The adsorption filter 44 can suitably contain activated charcoal, e.g. coconut shell charcoal. The order of membrane 42, valve 40 and filter 44 is not critical.

Additional safety in both the dosing of liquid anaesthetic and patient safety in general can be achieved by placing an anaesthetic meter 46 downstream from the dosing point 14.

In contrast to the flow meter 26, which measures the actual flow of liquid anaesthetic, the anaesthetic meter 46 measures the concentration of anaesthetic in the gas mixture flowing through the tube 4. Two faults may be present when the measured concentration deviates from a reference value for the concentration (apart from faults in the meter(s)). One fault could be erroneous dosing of anaesthetic. The other could be an erroneous flow of the gas mixture in the tube 4.

Regardless of which fault is involved, the anaesthetic vaporizer 2 can react immediately to excessive concentrations of anaesthetic by closing the shut-off valve 24. Like the safety concept behind the flow meter 26, this safety system can be incorporated into the control unit 36 as a completely separate unit.

Alternatively, the measurement signal from the anaesthetic meter 46 can be used for further refining dosing of the anaesthetic. If the flow of the gas mixture does not deviate too much from the desired flow (and reaches a flow sufficient to assure the patient's safety), dosing can be adjusted with the aid of the measured concentration. At the same time, an alarm should still be activated or a warning issued to the operator whenever any deviations occur which have an impact on the system's performance and/or patient safety.

FIG. 1 also shows a pressure stabilizer 48 connected to the outlet tube downstream from the first connection point 30. The purpose of the pressure stabilizer 48 is to facilitate maintenance of the working pressure. The pressure stabilizer 48 can be a bellows or some other variable-volume container and be loaded with a spring, piston or some other pressure-exerting component. Pressure loading of the bellows preferably should be adjustable so loading can be set at the working pressure. The volume of the pressure stabilizer 48 can be dimensioned for the volumes to be dosed.

It should be noted that only the pump 18, the dosing valve 22 and the back-flow constrictor 34 are essential to the dosing function of the anaesthetic vaporizer.

Figure 2:
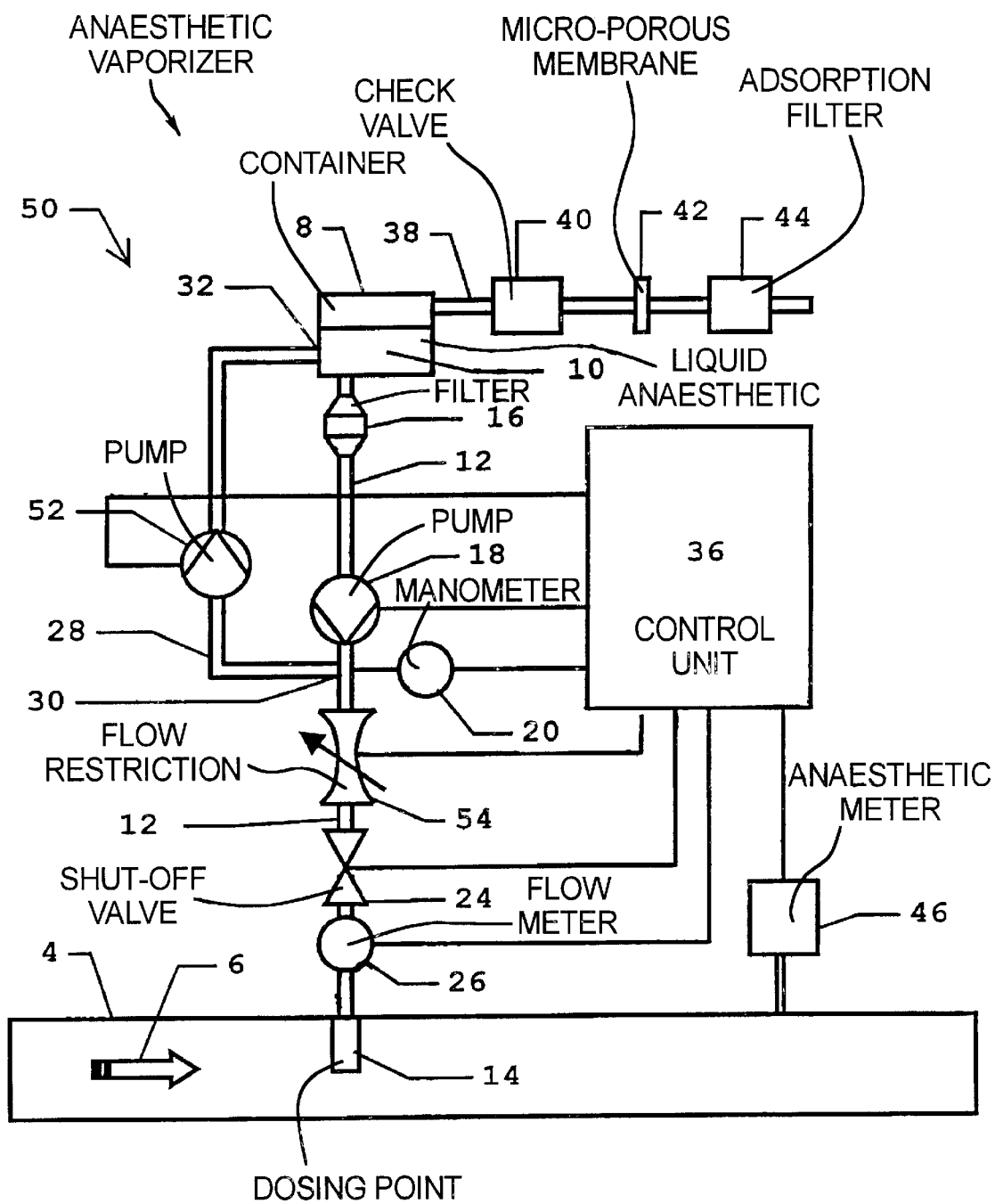
FIG. 2 shows a second embodiment of the inventive anaesthetic vaporizer.

A second embodiment of the anaesthetic vaporizer according to the invention is shown in FIG. 2 and is designated 50. All the components that are identical to those in the first embodiment have been assigned the same designations.

Thus, the anaesthetic vaporizer 50 has a liquid container 8 holding liquid anaesthetic 10. An outlet tube 12 connects the liquid container 8 to a dosing point 14.*)

*)The liquid container 8 could be a small container being constantly refilled by a bottle (not shown) attached to the container 8. The container 8 could even be a bottle containing liquid anaesthetic 10.

A filter 16, a pump 18, a shut-off valve 24 and a flow meter 26 can be arranged in the outlet tube 12.

A return tube 28 is arranged in parallel across the pump 18 between a first connection point 30 and a second connection point 32. In this embodiment, the second connection point 32 is arranged at the liquid container 8. A specific advantage here (in relation to the first embodiment) is the complete elimination of air bubbles from the part of the system to be filled with liquid.

A venting device, formed by a venting tube 38, a valve 40, a membrane 42 and a filter 44, is connected to the liquid container 8.

An anaesthetic meter 46 is connected for measuring the concentration of anaesthetic in the gas mixture.

A control unit 36 controls dosing of liquid anaesthetic by the anaesthetic vaporizer 50 into the gas mixture in a tube 4.

The main difference compared to the first embodiment is that an additional pump 52 is provided in the return tube 28 instead of a restriction. The second connection point 32 opens into the liquid container 8 instead of the outlet tube 12.

The dosing valve has been replaced with a dosing restriction 54. The dosing restriction 54 can be variable.

When the dosing restriction 54 is fixed, dosing can be achieved by varying the pressure of the liquid anaesthetic immediately upstream from the dosing restriction 54. The flow characteristics of the dosing restriction 54 at different pressures naturally must be known, but this is easily determined by experimentation.

When the dosing restriction 54 is variable, regulation of dosing with greater accuracy becomes possible, even if complexity increases.

As the above shows, there are many versions of available regulating methods for the anaesthetic vaporizer according to the invention. They also can be complemented in other ways. For example, more filters can be arrayed to ensure function. Thus, one filter can be located immediately downstream from the first connection point 30. This filter blocks any particles from the pump 18.

The important feature of the invention which makes improved dosing and safety possible, is the configuration with two regulator (e.g. a pump and a valve, a valve and a valve or a valve and a restriction) with return via a third regulator (e.g. a pump, valve or restriction).

Although modifications and changes may be suggested by those skilled in the art, it is the intention of the inventors to embody within the patent warranted hereon all changes and modifications as reasonably and properly come within the scope of their contribution to the art.

We claim as our invention:

1. An anaesthetic vaporizer for dosing a liquid anaesthetic, comprising:
    a container containing a liquid anaesthetic;
    an outlet tube proceeding from said liquid container to a dosing point for said liquid anaesthetic;
    a first regulator for regulating a flow of said liquid anaesthetic from said liquid container toward said dosing point;
    a return tube connected in parallel across said first regulator between a first connection point downstream from said first regulator and second connection point upstream from said first regulator;
    a second regulator connected in said return tube;
    a third regulator connected in said outlet tube downstream from said first connection point; and
    a control unit for controlling at least one of said first regulator, said second regulator and said third regulator to control dosing of said liquid anaesthetic at said doing point.

2. An anaesthetic vaporizer as claimed in claim 1 wherein said first regulator comprises a first pump, said second regulator comprises a second pump, said third regulator comprises a flow restriction in said outlet tube, and further comprising a manometer connected between said first pump and said flow restriction for supplying a signal to said control unit for use in controlling dosing of said liquid anaesthetic.

3. An anaesthetic vaporizer as claimed in claim 2 wherein said flow restriction in said outlet tube is a variable flow restriction.

4. An anaesthetic vaporizer as claimed in claim 1 wherein said first regulator comprises a pump, said second regulator comprises a back-flow restriction in said return tube, and wherein said third regulator comprises a dosing valve, and further comprising a manometer connected between said pump and said dosing valve for supplying a signal to said control unit for use in regulating dosing of said liquid anaesthetic.

5. An anaesthetic vaporizer as claimed in claim 4 wherein said back-flow restriction comprises a variable back-flow restriction.

6. An anaesthetic vaporizer as claimed in claim 1 further comprising a venting device connected to said container.

7. An anaesthetic vaporizer as claimed in claim 1 further comprising a flow sensor connected in said outlet tube, downstream from said first connection point, for supplying a signal to said control unit for use in controlling dosing of said liquid anaesthetic.

8. An anaesthetic vaporizer as claimed in claim 1 further comprising a pressure stabilizer for said outlet tube disposed downstream from said first connection point.

9. An anaesthetic vaporizer as claimed in claim 1 further comprising an anaesthetic meter connected downstream from said dosing point for measuring an amount of anaesthetic dispensed from said dosing point and for providing a feedback signal to said control unit for use by said control unit in controlling dosing of said liquid anaesthetic.

10. An anaesthetic vaporizer as claimed in claim 1 further comprising a shutoff valve connected in said outlet tube downstream from said third regulator.

\* \* \* \* \*